United States Patent [19]

Bugante

[11] 4,067,717

[45] Jan. 10, 1978

[54] METHOD OF PROMOTING THE FLOWERING OF GRAPE VINES

[75] Inventor: Restituto L. Bugante, Makati, Philippines

[73] Assignee: Alfonso G. Puyat, Makati, Philippines

[21] Appl. No.: 729,732

[22] Filed: Oct. 5, 1976

[51] Int. Cl.² ............................................. C05D 3/02
[52] U.S. Cl. ................................................ 71/63; 71/1; 71/31; 71/32; 71/54; 71/61
[58] Field of Search ..................... 71/1, 31, 32, 34, 47, 71/53, 54, 61, 63, 64 C; 423/430

[56] References Cited

U.S. PATENT DOCUMENTS

| | | | |
|---|---|---|---|
| 1,320,701 | 11/1919 | Manns | 71/63 |
| 1,875,281 | 8/1932 | Von Sigmund | 71/63 |
| 2,061,534 | 11/1936 | Balz et al. | 71/63 X |
| 2,770,538 | 11/1956 | Vierling | 71/53 X |
| 3,660,069 | 5/1972 | Backlund | 71/53 X |
| 3,997,320 | 12/1976 | Bugante | 71/63 |
| 4,001,002 | 1/1977 | Barba | 71/65 |

*Primary Examiner*—Wilbur L. Bascomb, Jr.
*Assistant Examiner*—Ferris H. Lander

[57] ABSTRACT

This invention relates to a method of promoting the flowering of grape vines.

5 Claims, No Drawings

METHOD OF PROMOTING THE FLOWERING OF GRAPE VINES

This invention relates to a method of promoting the flowering of grape vines and is more particularly directed to the application of the novel composition disclosed in my U.S. Patent application Ser. No. 616,355 filed Sept. 24, 1975, now U.S. Pat. No. 3,997,320, Dec. 14, 1976.

The subject matter of the present invention is related to my earlier filed application Ser. No. 616,355 entitled "METHOD OF FLOWERING MANGO TREES AND COMPOSITION USED THEREFOR" which discloses a composition for promoting the flowering of mango trees which comprises:

A. from about 7 to 15% by weight of a salt of calcium selected from the group consisting of calcium hydroxide and calcium carbonate;
B. from about 0.06 to 0.08% by weight potassium hydroxide;
C. from about 0.05 to 0.07% by weight phosphoric acid;
D. from about 15.00 to 25.00% by weight nitric acid;
E. from about 0.005–0.007% by weight ammonium hydroxide;
F. from about 0.001–0.006% by weight manganese sulfate;
G. from about 0.006–0.10% by weight ferrous sulfate;
H. from about 0.00002 to 0.003% by weight zinc sulfate;
I. from about 0.15 to 0.35% by weight magnesium sulfate; and
J. balance water;

and to a method of promoting the flowering of mango trees which comprises applying to the leaves and terminal dormant buds an effective amount of the composition herein above described.

Conventional method of inducing flowering of grape vines of the variety Red Cardinal, Black Bevier, San Jose, Italian Obed and YSP alias Lady Finger show bud emergence only 12 to 15 days after prunning.

In view of the great demand for grapes, it is of great significance to increase the yield at a minimum time and at a lower cost.

It is the primary object of the present invention to provide a method of promoting flowering of grape vines using the hereinabove described compostion.

Further, it is an object of the present invention to provide a method of inducing flowering of grape vines which will attain much higher yield of grapes.

These objects as well as other objects of this invention will become readily apparent after reading the following description hereinafter disclosed.

According to the present invention, flowering of grape vines are induced by the application of effective amounts of the flower inducer composition disclosed in my related application at an appropriate time prior to harvest. In addition, application of the inducer composition assures that maximum yield will be obtained despite possible unfavorable weather conditions occuring prior to harvesting.

The amount effective to promote flowering is 1 part of the composition to 20-60 parts water depending on the average temperature. The hotter the temperature is, the more the dilution.

The present composition that is used in flowering grapes which has been used previously in flowering mango consists of the following:

|    |                          | % by weight |    |         |
|----|--------------------------|-------------|-----|---------|
| A. | calcium hydroxide or calcium carbonate | 7       | to  | 15%     |
| B. | potassium hydroxide      | 0.06        | to  | 0.08%   |
| C. | Phosphoric acid          | 0.05        | to  | 0.07%   |
| D. | Nitric acid              | 15.00       | to  | 25.00%  |
| E. | Ammonium hydroxide       | 0.005       | to  | 0.0007% |
| F. | Manganese sulfate        | 0.001       | to  | 0.006   |
| G. | Ferrous sulfate          | 0.006       | to  | 0.10    |
| H. | Zinc sulfate             | 0.00002     | to  | 0.003   |
| I. | Magnesium sulfate        | 0.15        | to  | 0.35    |
| J. | Balance water            |             |     |         |

The preparation of this composition is disclosed in my Philippine Pat. No. 8714 entitled "METHOD OF FLOWERING MANGO TREES AND COMPOSITION USED THEREFOR" issued on December 24, 1974.

One quart (946 ml) of the above composition is diluted with about 60 liters of water.

The following example illustrates further the invention. It is not to be construed as limiting the invention claimed hereinafter.

EXAMPLE

The above aqueous formulation is sprayed on the leaves and branches of 124 different varieties of grape vines which are 9 months old. Ten days after spraying the vines were pruned. Flower buds began to emerge from all the 124 vines three to four days after prunning. This is significant because usually, pruned grape vines that are not treated with the above aqueous formulation will show bud emergence only twelve to fifteen days after prunning.

The buds that came out were all physically observable after one week from prunning when the flower inducer was used.

Ten days after prunning, the leaves, branches, and even the newly formed flower buds of the grape vines are again sprayed with the aqueous formulation of the same concentration. Flower buds at this Stage per vine numbered between 60 to 80.

When the grape buds are big enough, 80% of the formed flower clusters must be aborted in order not to overburden the young vines. After aborting the excess flower clusters, the grapes can be treated with the usual pesticides, fungicides and other formulations prescribed for grape.

One hundred fifteen days after prunning, almost 240 kilos of grapes from the 124 vines are harvested.

After letting the vines rest for six months, similar results are obtained by using the same formuation at the same concentration.

In the foregoing example, the spraying was conducted anytime of the day even under the hot sun with no burning.

Also similar results are obtained by using the above composition at concentration of 1 is to 20 to 60.

I claim:

1. A method for promoting flowering of grape vines which comprises applying to the vines (leaves and branches) or to the flower buds, an effective amount of a composition comprising:

A. from about 7 to 15% by weight of a salt of calcium selected from the group consisting of calcium hydroxide and calcium carbonate;

B. from about 0.06 to 0.08% by weight potassium hydroxide;
C. from about 0.05 to 0.07% by weight phosphoric acid;
D. from about 15.00 to 25.00% by weight nitric acid;
E. from about 0.0005–0.0007% by weight ammonium hydroxide;
F. from about 0.001–0.006% by weight manganese sulfate;
G. from about 0.006–0.10% by weight ferrous sulfate;
H. from about 0.00002 to 0.003% by weight zinc sulfate;
I. from about 0.15 to 0.35% by weight magnesium sulfate; and
J. balance water.

2. A method according to claim 1 wherein the active composition is diluted to 1 part of the composition to 20–60 parts water.

3. A method according to claim 1 wherein the active composition is sprayed to 9 months old grape vines.

4. A method according to claim 1 wherein the active composition is sprayed prior to prunning of the grape vines.

5. A method according to claim 4 wherein the active composition is again sprayed after prunning.

* * * * *